(12) United States Patent  (10) Patent No.: US 7,972,281 B2
Fowler et al.                (45) Date of Patent:    Jul. 5, 2011

(54) LANCET SENSOR ASSEMBLY AND METER

(75) Inventors: James Fowler, Brewster, MA (US);
Robert Daggett, Chelmsford, MA (US);
Garland O'Connell, Newtonville, MA (US); James S. Sidwell, Boxborough, MA (US); Avi M. Robbins, Marietta, GA (US); Chris Ruf, Marietta, GA (US); Jeffrey T. Stout, Smyrna, GA (US)

(73) Assignee: Nova Biomedical Corporation, Waltham, MA (US)

( * ) Notice: Subject to any disclaimer, the term of this patent is extended or adjusted under 35 U.S.C. 154(b) by 0 days.

(21) Appl. No.: 12/758,404

(22) Filed: Apr. 12, 2010

(65) Prior Publication Data

US 2010/0191149 A1    Jul. 29, 2010

Related U.S. Application Data

(60) Division of application No. 11/426,950, filed on Jun. 28, 2006, now Pat. No. 7,727,167, which is a continuation-in-part of application No. 10/899,345, filed on Jul. 26, 2004, now Pat. No. 7,727,166.

(51) Int. Cl.
*A61B 5/00* (2006.01)
*A61B 17/14* (2006.01)
*A61B 17/32* (2006.01)
*B65D 81/00* (2006.01)
(52) U.S. Cl. ......... 600/583; 600/584; 606/181; 606/182
(58) Field of Classification Search .................. 600/583, 600/584; 606/181, 182
See application file for complete search history.

(56) References Cited

U.S. PATENT DOCUMENTS

| | | | | | |
|---|---|---|---|---|---|
| 3,760,809 | A | * | 9/1973 | Campbell, Jr. | 606/182 |
| 4,637,403 | A | * | 1/1987 | Garcia et al. | 600/583 |
| 4,677,979 | A | * | 7/1987 | Burns | 606/172 |
| 4,787,398 | A | * | 11/1988 | Garcia et al. | 600/583 |
| 4,869,249 | A | * | 9/1989 | Crossman et al. | 606/182 |
| 5,279,294 | A | * | 1/1994 | Anderson et al. | 600/322 |
| 5,314,441 | A | * | 5/1994 | Cusack et al. | 606/182 |
| 5,439,473 | A | * | 8/1995 | Jorgensen | 606/182 |
| 5,628,765 | A | * | 5/1997 | Morita | 606/182 |
| 5,755,733 | A | * | 5/1998 | Morita | 606/182 |

(Continued)

*Primary Examiner* — Max Hindenburg
*Assistant Examiner* — Sean P Dougherty
(74) *Attorney, Agent, or Firm* — Robert R. Deleault; Mesmer & Deleault, PLLC

(57) ABSTRACT

A method of obtaining a test sample from a specimen using a lancet system includes engaging a lancet driver against a drive wing of a lancet system, the lancet system having a major portion of a lancet member slidably engaged within a lancet carrier and a sensor strip with a sample chamber attached to the lancet carrier, the lancet system having a lance connected to a first end of a lancet body of the lancet member wherein the lance is movable from a retracted position within the lancet carrier to an extended position outside the lancet carrier, the drive wing extending outwardly and transversely from the lancet body, the major portion of the lancet member having a sinuous portion with a distal end restricted from movement by the lancet carrier, the sinuous portion being non-compressible when initially disposed within the lancet carrier wherein the drive wing prevents the sinuous portion from being compressed, moving the drive wing with the lancet driver a predetermined distance causing the lancet tip to move from the retracted position to the extended position, and disengaging the lancet driver from the drive wing, the lance being automatically moved from the extended position to the retracted position.

5 Claims, 19 Drawing Sheets

U.S. PATENT DOCUMENTS

| | | | | |
|---|---|---|---|---|
| 5,908,434 | A * | 6/1999 | Schraga | 606/181 |
| 5,971,941 | A * | 10/1999 | Simons et al. | 600/573 |
| 6,071,294 | A * | 6/2000 | Simons et al. | 606/181 |
| 6,299,626 | B1 * | 10/2001 | Viranyi | 606/182 |
| 6,306,152 | B1 * | 10/2001 | Verdonk et al. | 606/182 |
| 6,332,871 | B1 * | 12/2001 | Douglas et al. | 600/583 |
| 6,530,892 | B1 * | 3/2003 | Kelly | 600/583 |
| 6,561,989 | B2 * | 5/2003 | Whitson | 600/573 |
| 6,607,658 | B1 * | 8/2003 | Heller et al. | 205/777.5 |
| 6,620,112 | B2 * | 9/2003 | Klitmose | 600/583 |
| 6,958,072 | B2 * | 10/2005 | Schraga | 606/182 |
| 6,997,936 | B2 * | 2/2006 | Marshall | 606/181 |
| 7,223,248 | B2 * | 5/2007 | Erickson et al. | 600/584 |
| 7,299,081 | B2 * | 11/2007 | Mace et al. | 600/345 |
| 7,381,184 | B2 * | 6/2008 | Funderburk et al. | 600/300 |
| 7,481,818 | B2 * | 1/2009 | Allen et al. | 606/181 |
| 2001/0039387 | A1 * | 11/2001 | Rutynowski et al. | 600/573 |
| 2002/0040230 | A1 * | 4/2002 | Kuhr et al. | 606/181 |
| 2002/0052618 | A1 * | 5/2002 | Haar et al. | 606/181 |
| 2002/0082522 | A1 * | 6/2002 | Douglas et al. | 600/583 |
| 2002/0177761 | A1 * | 11/2002 | Orloff et al. | 600/309 |
| 2003/0050573 | A1 * | 3/2003 | Kuhr et al. | 600/567 |
| 2003/0050656 | A1 * | 3/2003 | Schraga | 606/182 |
| 2003/0083685 | A1 * | 5/2003 | Freeman et al. | 606/181 |
| 2003/0083686 | A1 * | 5/2003 | Freeman et al. | 606/181 |
| 2003/0144608 | A1 * | 7/2003 | Kojima et al. | 600/583 |
| 2003/0171696 | A1 * | 9/2003 | Dosmann | 600/583 |
| 2004/0064068 | A1 * | 4/2004 | DeNuzzio et al. | 600/583 |
| 2004/0186394 | A1 * | 9/2004 | Roe et al. | 600/583 |
| 2004/0225311 | A1 * | 11/2004 | Levaughn et al. | 606/181 |
| 2005/0101981 | A1 * | 5/2005 | Alden et al. | 606/181 |
| 2005/0149090 | A1 * | 7/2005 | Morita et al. | 606/181 |
| 2005/0177183 | A1 * | 8/2005 | Thorne et al. | 600/167 |
| 2005/0277850 | A1 * | 12/2005 | Mace et al. | 600/584 |
| 2006/0253146 | A1 * | 11/2006 | Marshall et al. | 606/182 |
| 2007/0185515 | A1 * | 8/2007 | Stout | 606/181 |
| 2008/0294064 | A1 * | 11/2008 | Calasso et al. | 600/547 |

* cited by examiner

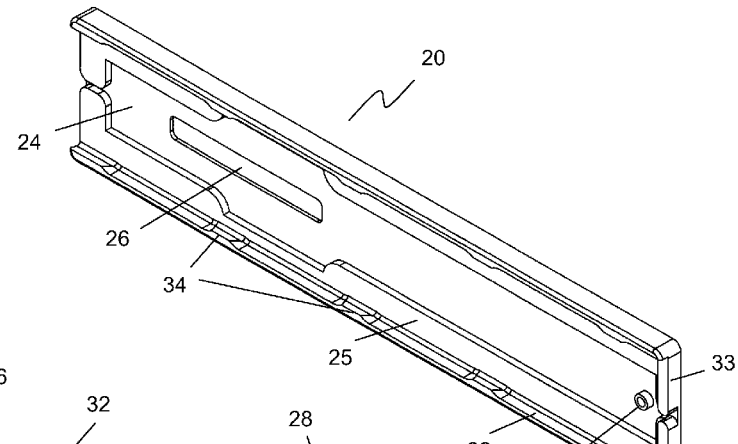
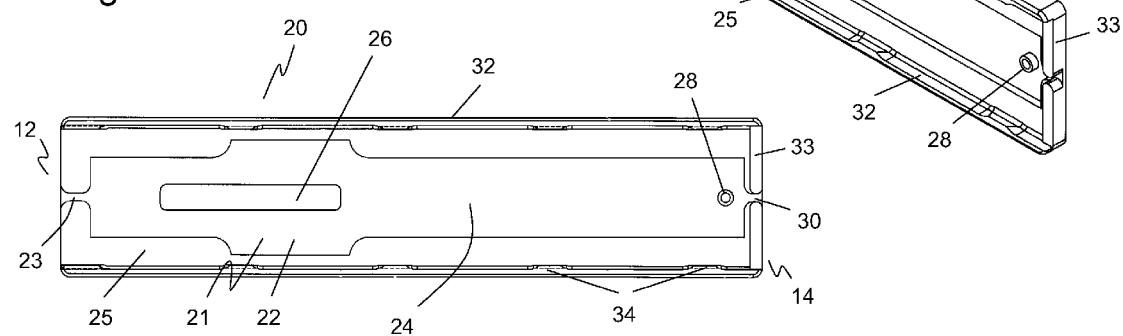
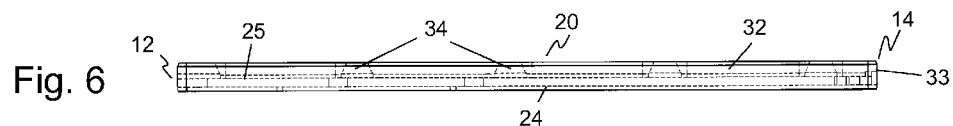

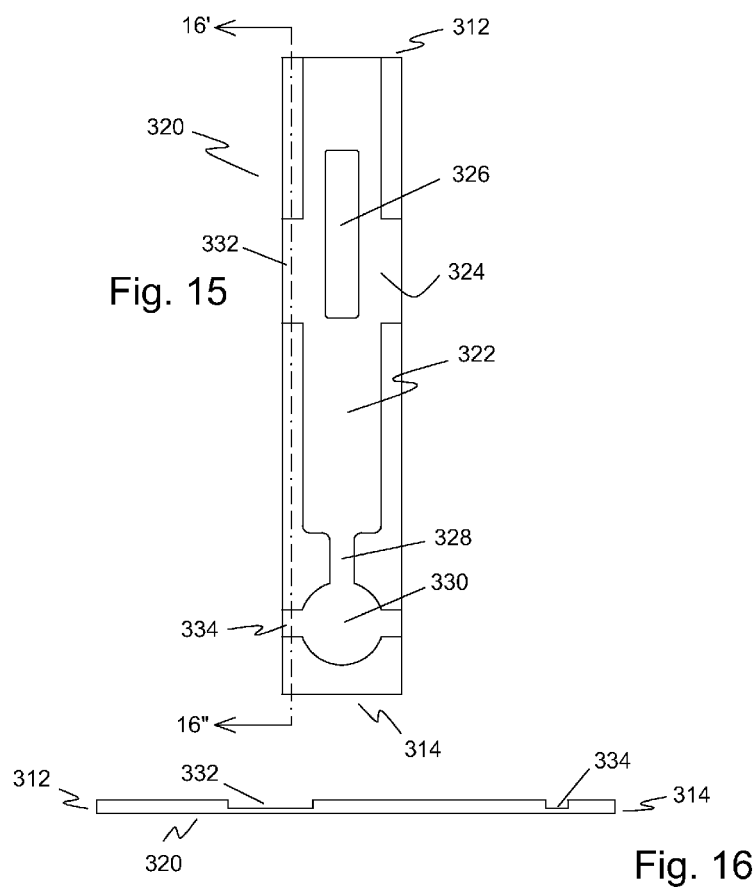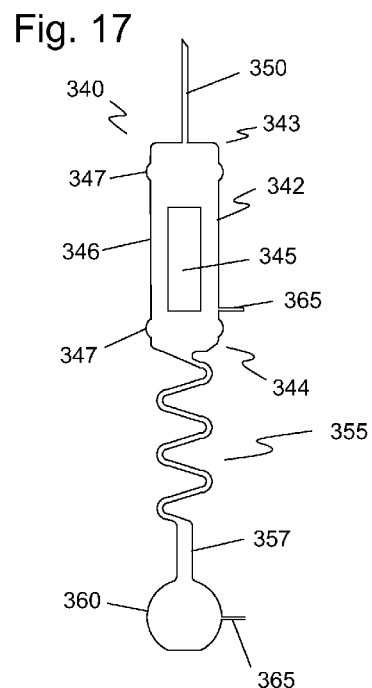

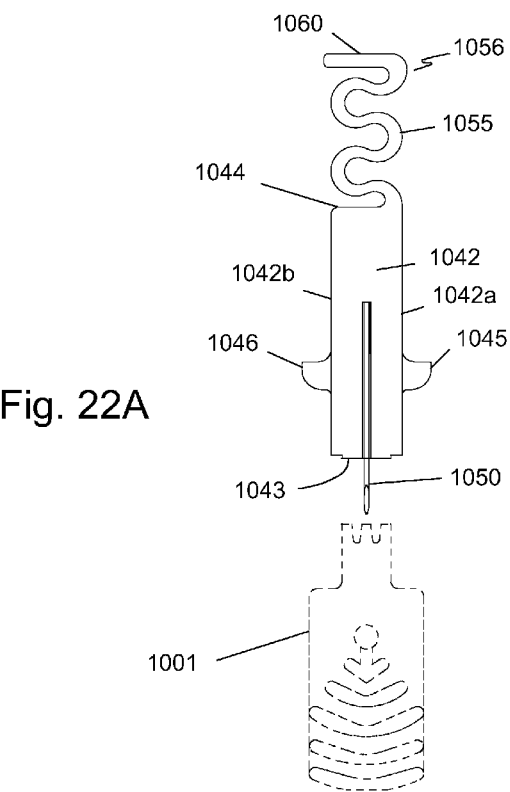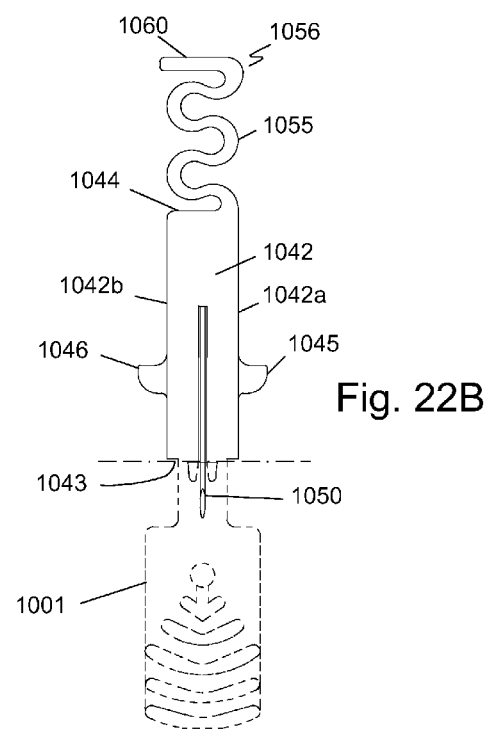

LANCET SENSOR ASSEMBLY AND METER

This application is a Divisional Application of Ser. No. 11/426,950, now U.S. Pat. No. 7,727,167 filed Jun. 28, 2006, which is a Continuation-in-Part Application of Ser. No. 10/899,345, filed on Jul. 26, 2004 now U.S. Pat. No. 7,727,166.

BACKGROUND OF THE INVENTION

1. Field of the Invention

The present invention relates generally to testing body fluids. Particularly, the present invention relates to a lancet used for obtaining a sample of body fluid for testing. More particularly, the present invention relates to a lancet and test strip combination. Still more particularly, the present invention relates to a diagnostic system incorporating a lancet and test strip combination and an electronic meter.

2. Description of the Prior Art

The examination of blood samples in clinical diagnostics enables the early and reliable recognition of pathological states as well as a specific and well-founded monitoring of physical condition. Lancets and lancet devices enable blood sample collection especially for home monitoring by diabetics.

A blood sugar level that is either too high or low can lead to adverse physical consequences for a diabetic. Personal blood sugar determination is important for diabetics to aid in controlling and maintaining blood sugar levels with the use of insulin and other medications. A lancet is used to pierce the skin (usually a finger) and produce a small blood sample. Lancing the skin is painful. For diabetics who are required to test their blood sugar level several times a day, lancing several times a day is a painful but necessary procedure. The blood sample is then placed on a test strip for analysis and the blood glucose level is read by a blood glucose meter. Various devices have been devised for lancing the skin of a user as well as combination devices that include lancets and analytical device.

U.S. Pat. No. 6,620,112 (2003, Klitmose) discloses a disposable lancet combined with a reagent carrying strip which carries a reagent that indicates the concentration of a blood component in a blood sample placed in contact with the strip. The reagent carrying strip is connected to the lancet, e.g. by molding. One end of the lancet is sharpened for piercing the skin. The strip is sheet-like and has a first side and a second side, which sides are both accessible for the user, such that the reagent carrying strip can be inserted into a blood glucose meter. A weakened tear line is provided at a connection between the lancet and an edge of the reagent carrying strip so that the reagent carrying strip may be easily disconnected from the lancet.

U.S. Patent Application Publication No. US2003/0050573 (Kuhr et al.) discloses an analytical device containing a lancet comprising a lancet needle and a lancet body, the lancet needle being movable relative to the lancet body and the lancet body being composed, at least in the area of the tip of the lancet needle, of an elastic material in which the tip of the lancet needle is embedded, and an analytical test element which is permanently connected to the lancet body. In addition the invention concerns an analytical device containing a lancet comprising a lancet needle and lancet body which is in the form of a hollow body in the area of the tip of the lancet needle and surrounds the tip of the lancet needle, the lancet needle being movable relative to the lancet body and the hollow body being composed at least partially of an elastic material, and an analytical test element which is permanently connected to the lancet body.

U.S. Pat. No. 6,607,658 (2003, Heller et al.) discloses an analyte measurement device includes a sensor strip combined with a sample acquisition device to provide an integrated sampling and measurement device. The sample acquisition device includes a skin piercing member such as a lancet attached to a resilient deflectable strip which may be pushed to inject the lancet into a patient's skin to cause blood flow. The resilient strip is then released and the skin piercing member retracts.

U.S. Patent Application Publication No. 2002/0130042 (Moerman et al.) discloses an apparatus having a meter unit, a lancet and an electrochemical sensor. The meter is reusable while the lancet and the electrochemical sensor are incorporated into assemblies intended for single use. The meter has a housing within which a lancet is engaged with a mechanism for moving the lancet, a connector disposed within the housing for engaging an electrochemical sensor specific for the analyte, and a display operatively associated with a connector for displaying the amount of the analyte to the user.

U.S. Patent Application Publication No. 2002/0082522 (Douglas et al.) discloses a device and method for lancing a patient, virtually simultaneously producing and collecting a small fluid sample from the body. The device includes a lancing needle, drive mechanism, kneading or vibration mechanism, optional suction system, and sample ejection mechanism.

A disadvantage of the above prior art is that each of the lancets are rigid and rely solely on the spring action of a firing mechanism to retrieve the lancet after firing or, in the case of the Heller device, the specimen piercing speed of the lancet is uncontrolled and depends on the quickness of the user. Further, the prior art that provides for shallow depth penetration of the lancet generally includes a sophisticated system to knead the surrounding lanced area by ultrasonic action, piezo-electric or mechanical oscillation to stimulate the blood flow from the wound to draw the blood into a pumping system. It should also be noted that none of the prior art lancet sensor combination devices are currently available in the marketplace, which indicates that the prior art devices do not provide a reasonable, cost-effective, useful, and workable system for a lancet sensor combination test strip and meter.

Currently available, prior art, blood glucose meters include those known as the Accu-Chek® Aviva system by Roche Diagnostics, the One-Touch® system by LifeScan, the Glucometer® DEX system by Bayer, the True Track® system by Home Diagnostics, and the Freestyle® system by Abbott. Although these meters advertise various advantages such as fast and reliable test results, small volume requirements and reduced pain systems, each of the currently available meters requires the use of a separate lancing device to obtain the blood sample from the patient. Some require the occasional use of a control reagent to calibrate the meter. All, however, require a patient to carry both the meter and the lancing device with the appropriate number of disposable test strips and lancets. None of these currently available meters, on the other hand, are capable of accepting a combination lancet sensor test strip or eliminating the need for a separate lancing device.

Therefore, what is needed is a lancet assembly that has an inherent return action upon piercing a specimen. What is further needed is a lancet assembly that can incorporate an analytical test strip. What is also needed is a test strip diagnostic, handheld meter that is capable of driving a lancing device and electronically testing a blood sample. What is still needed is a diagnostic, handheld meter that is usable with a lancet sensor test strip combination.

SUMMARY OF THE INVENTION

It is an object of the present invention to provide a lancet assembly that has an inherent return action upon piercing a specimen. It is another object of the present invention to provide a lancet assembly capable of incorporating an analytical test strip forming a disposable, integrated unit. It is a further object of the present invention to provide a diagnostic, handheld meter that is capable of driving a lancing device and electronically testing a blood sample. It is still another object of the present invention to provide a diagnostic, handheld meter that is usable with a lancet sensor test strip combination. It is yet another object of the present invention to provide a blood glucose diagnostic system that provides fast, reliable results and is virtually pain free when obtaining a blood sample.

The present invention achieves these and other objectives by providing each of the following: a lancet assembly having at least a lancet, a lancet assembly having at least a lancet and an elongated carrier for holding the lancet; a lancet sensor combination test strip assembly; a diagnostic, handheld meter incorporating measuring circuitry and a lancing mechanism for use with a lancet sensor combination test strip assembly; and a portable glucose test system that includes a lancet sensor strip assembly and a diagnostic, handheld meter.

In one embodiment of the lancet of the lancet assembly, the lancet includes a lancet body, a lancet tip, a sinuous portion, and an anchor portion. Lancet body has a lancet tip end, a sinuous portion end, and a lancet slot. The lancet slot receives a lancet driver for driving the lancet tip and lancet body from a retracted position to an extended position. Lancet assembly may optionally include a lancet enclosure for receiving the lancet.

The lancet enclosure is an elongated structure with a needle end and an anchor end, a surface with a recess for receiving the lancet, and a bottom with a lancet enclosure slot spaced from the needle end. In one embodiment, the recess has a narrower portion at the needle end through which the lancet tip is guided to the outside of the lancet enclosure. At the anchor end, there is configured a system to anchor one end of the lancet relative to the lancet enclosure. The lancet enclosure slot in the bottom is longer than the lancet slot to accommodate the extension of the lancet out of the lancet enclosure. The lancet enclosure also includes extended sides for receiving a cover or for direct attachment to a holder. The cover is in a layered relationship with the lancet.

In another embodiment of the lancet enclosure, the recess has a first recess portion extending from the needle end, a bottom with a lancet enclosure slot spaced from the needle end, a second recess portion that is narrower than the first recess portion and which extends from the first recess portion opposite the needle end, and a third recess portion that is wider than the second recess portion and which extends from the second recess portion. Optionally, the lancet enclosure may have a plurality of first side openings and a plurality of second side openings to accommodate optional side tabs on the lancet that may be created during the manufacturing process.

In either embodiment, the depth of the recess in the lancet enclosure is deeper than the thickness of the lancet so that the lancet body can freely move the lancet tip out of the needle end from a retracted position to an extended position and back to the retracted position.

In another embodiment of the lancet of the lancet assembly, the lancet includes a lancet body, a lance extending from the lancet body on one end, a sinuous portion extending from the lancet body on an opposite end, and a drive wing extending outwardly from a side of the lancet body. The lance may be flat, round or any shape commonly used as a lancet for lancing the skin. The sinuous portion has a distal end with an anchor portion. The lancet body may optionally include a second drive wing extending outwardly from the side opposite of the first drive wing.

The elongated carrier includes a lancet receiving recess, an open end that is also the needle end, a closed end, a first side, a second side, a first side opening, an optional second side opening, an anchor mechanism, and an assembly retaining mechanism. The first and second sides include supporting edges for supporting an optional lancet assembly cover or a sensor test strip. The assembly retaining mechanism is a plurality of tabs that can be bent over the recess or deformed to retain the lancet within the elongated carrier. The first side opening is elongated to allow the drive wing to extend outside of the elongated carrier in position to cooperate with a lancet driver. The elongated side opening allows the drive wing, lancet body and lance to slide between a retracted position and an extended position. The drive wing is initially positioned within the elongated side opening such that the drive wing prevents the sinuous portion of the lancet from being compressed when the lance is in an initial position disposed within the elongated carrier. The anchor mechanism engages the anchor portion of the lancet to prevent the distal end of the sinuous portion from moving when the drive wing is engaged to cause the lancet to slide to the extended position. The elongated carrier may optionally include side notches or slots near the closed end to enhance retention of the lancet assembly when inserted into a meter or lancing device.

In one embodiment, the lancet carrier is made of metal and has a plurality of bendable tabs and an optional bottom groove. The metal elongated carrier is stamped, cut and bent to the desired shape. The optional bottom groove is formed by stamping and creates a rib along the outside surface of the bottom. The optional bottom groove/rib provides not only stability to the elongated carrier but also serves as a guide when inserting the lancet assembly into a meter/lancing device. In another embodiment, the lancet carrier is made of plastic that allows for molding/thermoforming the lancet carrier.

In both lancet assembly embodiments, the elongated carrier may optionally include one or more wing guards that extend away from the side of the elongated carrier in the vicinity of the elongated side opening where the drive wing is located. The wing guard protects the drive wing of the lancet from being inadvertently hit when being handled by a user and/or inserted to a meter or lancing device. Furthermore, the depth of the recess in the lancet carrier is deeper than the thickness of the lancet so that the lancet body can freely move the lancet tip out of the needle end from a retracted position to an extended position and back to the retracted position.

In another embodiment of the present invention, the lancet assembly may optionally include a test strip attached to the top side of the lancet carrier. The test strip typically includes a sample fluid entrance port, a sample chamber with at least one sensor and a sample vent hole. Electrical contacts are situated at the opposite end of the test strip for connecting to a meter.

A lancet gun device may also be optionally included. The lancet gun device includes a housing, a lancet penetration gauge, a lancet assembly receiver for receiving a lancet, a lancet drive mechanism, an activating member, and a trigger.

The lancet penetration gauge includes a plurality of recesses each having a different depth and is designed to cooperate with a lancet drive mechanism stop for regulating the penetration depth of the lancet tip. The housing includes rails having a first rail portion and a second rail portion offset from the first rail portion as well as a lancet driver slot configured to align with the lancet slot.

In one embodiment of the lancet gun device, the lancet drive mechanism has a stop rod with a lancet penetration gauge disposed at one end of the lancet gun device. In another embodiment, the lancet drive mechanism has a stop on a portion of the lancet drive mechanism that is engaged with one of the rail portions. The lancet penetration gauge in this embodiment is located along the side of the lancet gun device adjacent to the rail where the stop is located.

In still another embodiment, an optional diagnostic, handheld meter is included. The diagnostic, handheld meter has measuring circuitry, lancing driver assembly components and a test strip port incorporated into a meter housing. The measuring circuitry is preferably an electrochemical measuring circuit designed for using a particular electrochemical measuring method such as, for example, amperometric, coulometric, potentiometric, voltammetric, or other electrochemical techniques. A lancet sensor test strip socket is connected to the measuring circuitry to provide an electrical connection between the sensor strip and the measuring circuitry. The lancing driver assembly components include a lancet driver, a lancet trigger, a test strip receiver platform, and an optional lancing depth control.

The lancet trigger is an asymmetrical trigger. The asymmetrical trigger includes a trigger body that is typically secured to the meter housing, a lancet driver piston release positioned near the base of the trigger body, and a user interface positioned on a trigger arm that extends outwardly from the top of the trigger body. The user interface is located along the central axis of the meter, which also coincides with the central axis of the disposable lancet sensor test strip. It is the asymmetrical design of the trigger relative to the trigger body that allows the user interface to be located along the central axis of the meter and test strip port providing the user with easy and comfortable access to the firing trigger regardless whether the user is right-handed or left-handed. Because of the user interface's position along the central axis of the meter and the test strip port, it makes the lancing procedure easy and comfortable for the user. No other prior art device has this structure.

The test strip receiver platform supports the disposable lancet sensor test strip when it is inserted into the meter. The test strip receiver platform has two platform sides, a proximal end and a distal end. A portion of a first platform side at the proximal end is exposed at the test strip port. This makes it easy for the user to load and insert a disposable lancet sensor test strip. The distal end of the receiver platform includes a cross support with guide hooks on each end for cooperating with a charging member of the lancet driver. The first platform side includes a driver slot through which a lancet driver surface extends for engaging the drive wing of the lancet sensor test strip. The first platform side may also include a test strip guide groove when the test strip incorporates a mating guide rib. A second platform side slidingly supports a driver piston of the lancet driver.

The lancet driver includes a piston driver, a driver charging member, a piston drive spring, a pair of piston return springs, and a pair of charging member return springs. The piston driver has a piston body with a lancet driver surface located near a drive wing end, a drive spring recess for receiving the piston drive spring and a pair of return spring arms that extend away from the driver body. As mentioned above, the driver piston is slidingly supported by the second platform side of the test strip receiver platform with the lancet driver surface extending through the driver slot to the first platform side for engaging with the drive wing of the test strip. The piston drive spring is secured on one end within the drive spring recess while the other end contacts a central portion of the cross support of the test strip receiver platform. The central portion of the cross support acts as a stop surface for the drive spring when the driver piston is loaded into the "armed" position. The proximal end of the driver piston has a driver piston holding surface that cooperates with the driver piston release of the lancet trigger to hold the driver piston in the "armed" position until released by the user.

The driver charging member has a handle, a pair of parallel charging member rails that extend from the inside of the handle, charging member arms that extend perpendicularly from the inside of each of the charging member rails towards each other, a stop interface on one end of one of the charging member rails, and a pair of charging member return springs. Each of the charging member return springs connects on one end to the charging member rails and on the other end to the meter housing. Each of the charging member rails slidingly engages with one of the receiver platform side edges. The charging member arms also include a piston stop surface that is used to engage and arm the driver piston when the charging handle is pulled and to stop the sliding movement of driver piston when it is discharged from the armed position.

The meter housing may optionally include a lancing depth control. The lancing depth control has a detent side and a depth gauge side. The detent side includes a plurality of tabs extending out of the surface of the detent side with spaces between each of the plurality of tabs for receiving the detent. The tabs are relatively rigid but sufficiently flexible to allow the tabs to deflect and ride over the detent when the lancing depth control is changed. The depth gauge side has a charging member interface surface that is a gradual recessing surface that cooperatively engages the stop interface of the driver charging member to set the depth of lance penetration.

The portable glucose test system includes the handheld, portable meter capable of receiving a lancet sensor test strip, one or more disposable lancet sensor test strips, and an optional control solution. The handheld meter provides, in a single instrument, the dual functionality of driving a lance from the lancet sensor test strip to pierce a lancing site to obtain a sample and to perform the necessary electrochemical measurement steps to determine the concentration of glucose in the sample when it is added to the sample chamber of the sensor strip. No additional, separate lancing device is required to perform the lancing step.

BRIEF DESCRIPTION OF THE DRAWINGS

FIG. 5 is a top view of the lancet enclosure of the embodiment shown in FIG. 1.

FIG. 6 is a side view of the lancet enclosure of the present invention shown in FIG. 5.

FIG. 7 is a perspective view of the lancet enclosure of the present invention shown in FIG. 5.

FIG. 15 is an enlarged top view of the lancet enclosure of the embodiment illustrated in FIG. 13.

FIG. 16 is an enlarged side view of the lancet enclosure of the embodiment illustrated in FIG. 15.

FIG. 17 is an enlarged top view of the lancet of the embodiment illustrated in FIG. 13.

FIGS. 22A and 22B are top views of the lancet of the embodiment shown in FIG. 20.

DETAILED DESCRIPTION OF THE PREFERRED EMBODIMENT

Figure 1:
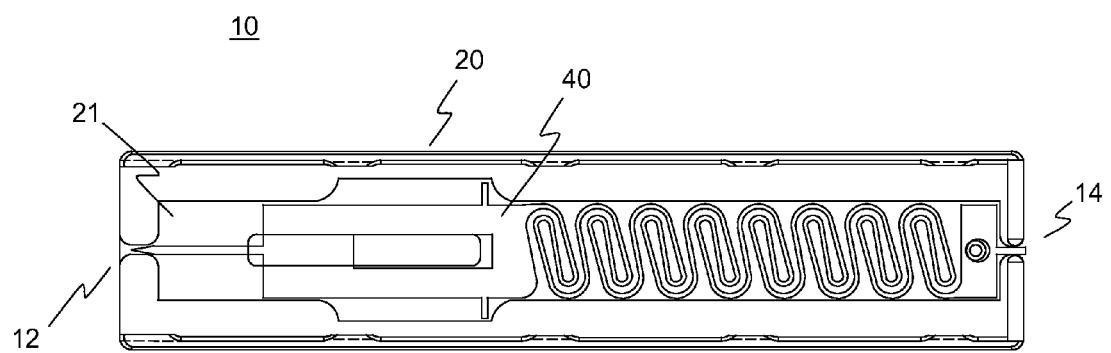
FIG. 1 is a top view of the preferred embodiment of the present invention showing a lancet within a lancet enclosure.

The preferred embodiment(s) of the present invention are illustrated in FIGS. 1-32. FIG. 1 shows a lancet assembly 10 of the preferred embodiment of the present invention. Lancet assembly 10 includes a lancet enclosure 20 and a lancet 40. Lancet enclosure 20 includes a recess 21 that is configured to receive and contain lancet 40 when lancet assembly 10 is in a static state. Lancet assembly 10 has a needle end 12 through which lancet 40 protrudes and retracts during use and an anchor end 14. A separate lancet cover (not shown) or a test strip (discussed later) may optionally be included, but is not necessary, with the lancet enclosure 20. Lancet enclosure 20 may be made of a plastic material such as, for example, polyvinyl chloride, polycarbonate, polysulfone, nylon, polyurethane, cellulose nitrate, cellulose propionate, cellulose acetate, cellulose acetate butyrate, polyester, acrylic, and polystyrene.

Figure 2:
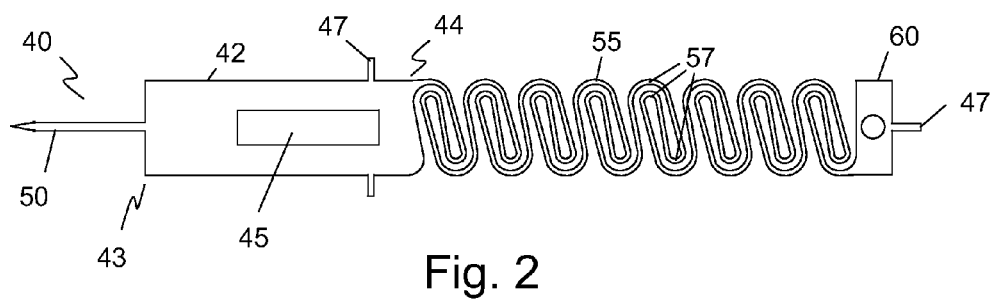
FIG. 2 is a top view of the lancet of the present invention shown in FIG. 1.

FIG. 2 shows an enlarged top view of lancet 40. Lancet 40 includes a lancet body 42, a lancet tip 50, a sinuous portion 55, and an anchor portion 60. Lancet body 42 has a lancet tip end 43, a sinuous portion end 44, and a slot 45. Slot 45 is configured to align with slot 26 of lancet enclosure 20 but is shorter than slot 26. This ensures sufficient clearance for a lancet driver to operate properly in conjunction with lancet assembly 10 during use. A lancet driver is inserted into slot 45 and drives lancet 40 to an extended position.

Sinuous portion 55 is a continuous strand of material having a plurality of loops 57. Sinuous portion 55 is connected on one end to lancet body 42 and to anchor portion 60. Lancet 40 may optionally have one or more tabs 47, which are the remnants of the connections between a plurality of lancets 40 formed during the manufacturing process. Lancet 40 is preferably made of a metal material such as, for example, stainless steel having a thickness of about 0.010 inches (0.254 mm). The thickness of lancet 40 must be thinner than the depth of recess 16 in lancet enclosure 20 to allow the protrusion and retraction of lancet tip 50. Lancet 40 may also be made of other materials such as, for example, plastics having sufficient rigidity to act as a lancet tip 50 for piercing skin but be resilient enough to provide the spring-like action of the sinuous portion 55.

Figure 3:
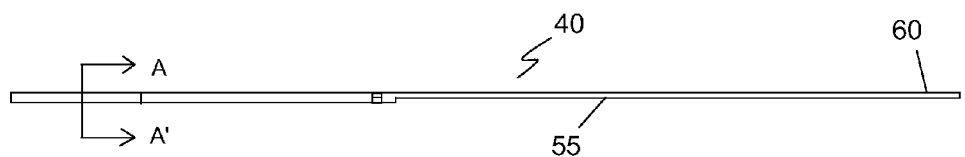
FIG. 3 is a side view of the lancet of the present invention shown in FIG. 2

FIG. 3 shows a side view of lancet 40 illustrated in FIG. 2. As can be seen from FIG. 3, sinuous portion 55 is thinner than lancet body 42 and lancet tip 50. Sinuous portion 55 is reduced in thickness to about 0.004 inches (0.102 mm). The reduction in thickness enhances the spring-like action of sinuous portion 55 in extending and retracting lancet tip 50 during use. The preferred method of reducing the thickness of sinuous portion 55 is by etching. Although it is illustrated that sinuous portion and anchor portion 60 are both etched to the same reduced thickness, it should be noted that anchor portion 60 may optionally not be etched since the thickness of anchor portion 60 has no bearing on the functionality of the sinuous portion 55.

Figure 3A:
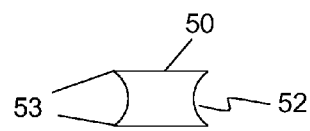
FIG. 3A is an enlarged cross-sectional view of along line A-A' in FIG. 3.

During the etching process to reduce the thickness of sinuous portion 55, a unique lancet tip design is created. FIG. 3A illustrates a cross-sectional view of lancet tip 50 taken along line A-A' in FIG. 3. Lancet tip 50 has a concave recess 52 along opposite sides forming a plurality of cutting edges 53. The formation of lancet tip 50 will now be explained.

Turning now to FIGS. 4a-4f, there is illustrated lancet tip 50 after the etching process and the shaped tip after grinding/lapping. It should be noted that the process used in forming lancet tip 50 produces a unique needle tip with a minimum of nine cutting edges. Like most typical etching processes, a mask is applied to the object to be etched. Before subjecting lancet 50 to the etching process, lancet tip 50 is shaped into a needle point forming an included angle θ of about fifteen degrees (15°).

In the present invention, an etching mask is applied to the bottom of lancet 40 while only a portion of the top of lancet 40 is masked. In the preferred embodiment, the top portion that includes the sinuous portion 55, anchor portion 60, and a portion of lancet body 42 at sinuous end 44 are not masked and neither are the sides and ends of lancet 40. Lancet 40 is then exposed to the etching process for a predetermined time in order to obtain a thickness of the sinuous portion 55 of about 0.004 inches (0.102 mm). After etching, the mask is removed from lancet 40.

Figure 4A:
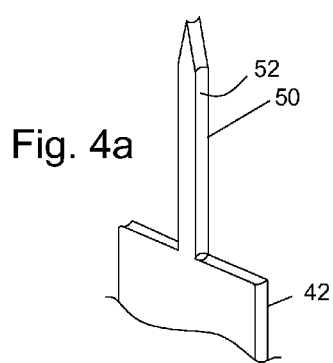
FIGS. 4a-4f are enlarged perspective, front and side views of the lancet cutting edges representing the method of forming the unique structure of the lancet.
Figure 4B:
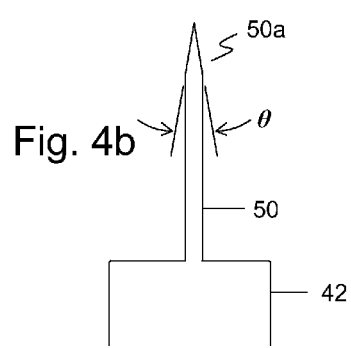
Figure 4C:
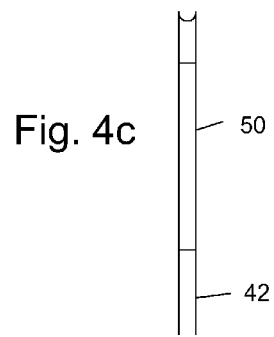

Turning now to FIG. 4a, there is illustrated a perspective view of lancet tip 50 with a portion of lancet body 42 as viewed from the bottom side of lancet 40. The etching process produces a concave-shaped side 52. FIG. 4b shows a bottom view of lancet tip 50 formed with angled end 50a having an angle θ. Angled end 50a may be obtained by various methods known to those of ordinary skill in the art. FIG. 4c illustrates a side view of lancet tip 50 with a concave shaped tip. To complete the formation of lancet tip 50, lancet tip 50 is shaped to an acute angle σ on the bottom side.

Figure 4D:
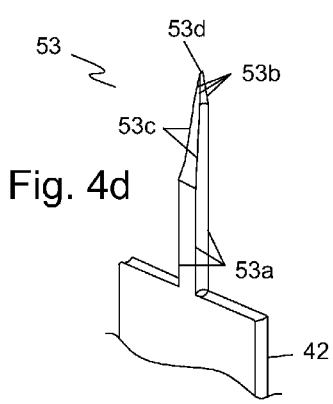
Figure 4E:
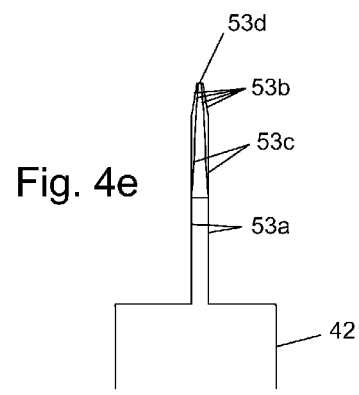
Figure 4F:
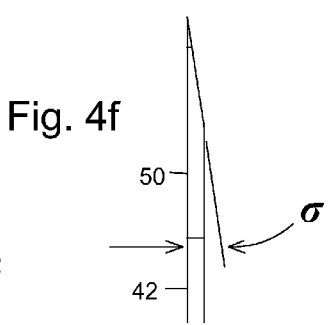

FIG. 4d illustrates a perspective view of a finished lancet tip 50 having angle σ formed on one side. As shown in FIG. 4d, a lancet tip 50 has a plurality of cutting edges 53. For this embodiment, the total number of cutting edges is eleven as a result of the formation of concave sides caused by the etching process. The cutting edges include four side edges 53a of lancet tip 50, the four edges 53b formed by the θ-angle, two edges 53c formed by the σ-angle, and the end edge 53d. FIG. 4e illustrates a bottom view of lancet tip 50 showing the relationship of the cutting edges. FIG. 4f illustrates the angle σ of lancet tip 50. Due to the size of lancet tip 50, a lapping technique instead of grinding is the preferred method of forming angle σ. Angle σ is an angle of about seven and one-half degrees (7.5°).

Turning now to FIG. 5, there is shown an enlarged top view of lancet enclosure 20 of the present invention. Lancet enclosure 20 has recess 21 having a lancet body recess portion 22 extending from a needle recess portion 23 at needle end 12, a bottom 24 with a slot 26 spaced from needle end 12, and an anchor structure 28 adjacent anchor end 14. Optionally, anchor end 14 may include a tab extension recess 30 for receiving a manufacturing tab 47 of lancet 40. In the preferred embodiment, anchor structure 28 is a protrusion extending away from lancet enclosure bottom 24 for anchoring lancet anchor portion 60. Optionally, lancet enclosure 20 may have side wall extensions 32 and an anchor end wall 33 for receiving a cover or a sensor strip or for attaching to a lancet gun device. In addition, side wall extensions 32 may optionally include a plurality of lancet enclosure retaining tabs 34. FIG. 6 illustrates a side view of lancet enclosure 20. The dashed lines indicate the recess bottom 24, recess top surface 25, and the side wall extension 32 and lancet enclosure retaining tabs 34. FIG. 7 illustrates a perspective view of lancet enclosure 20 and more clearly shows the recess bottom 24, the recess top surface 25, side wall extensions 32 with lancet enclosure retaining tabs 34. Typically, the thickness of lancet enclosure 20 is about 0.018 inches (0.457 mm), not inclusive of side wall extensions 32 which are about 0.022 inches (0.559 mm). The depth of recess 21 is typically 0.012 inches (0.305 mm).

Figure 8:
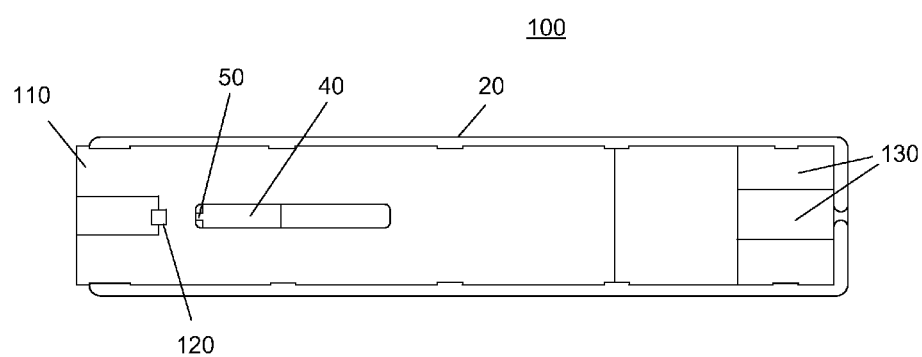
FIG. 8 is a top view of the present invention showing the combination of a lancet, sensor strip and lancet enclosure where the lancet is in a retracted position.
Figure 9:
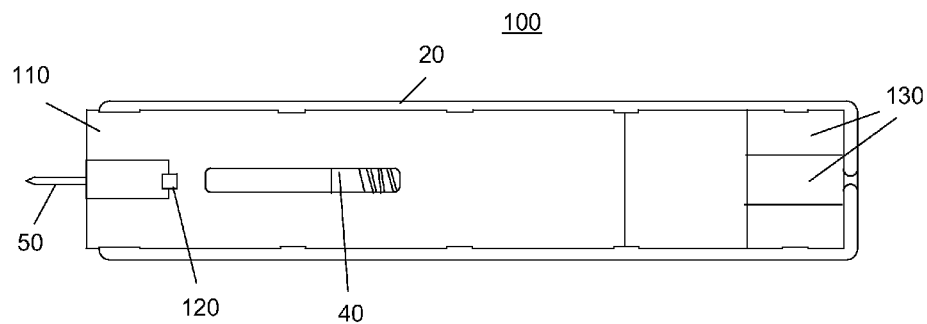
FIG. 9 is a top view of the present invention showing the combination of a lancet, sensor strip and lancet enclosure where the lancet is in an extended position.

Turning now to FIG. 8, there is illustrated an integrated lancet-test strip combination 100 that includes a test strip 110 attached to lancet assembly 10. Test strip 110 includes a sample fluid entrance port 112 (not shown), a sample chamber 114 (not shown) containing at least one sensor and a sample vent hole 120. Electrical contacts 130 are situated at the opposite end adjacent anchor end 14. Test strip 110 is preferably fixed to lancet assembly 10 forming an integrated lancet-test strip combination 100. Test strip 110 acts as a cover to recess 21 of lancet assembly 10 enclosing lancet 40 within lancet enclosure 20. FIG. 9 illustrates the integrated lancet-test strip combination embodiment of FIG. 8 where the lancet 40 is in an extended position with lancet needle 50 outside of lancet enclosure 20.

Figure 10:
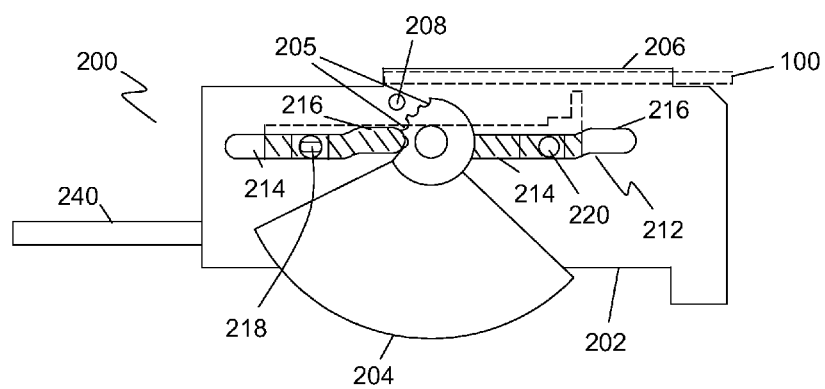
FIG. 10 is a side view of one embodiment of a lancet gun device showing a side mounted lancet penetration gauge.

Lancet 40 requires the use of a lancet drive mechanism in order to drive the lancet tip 50 into its destination. One embodiment of such a driving mechanism is illustrated in FIG. 10. FIG. 10 shows a side view of a lancet gun device 200. Lancet gun device 200 includes a housing 202, a lancet penetration gauge 204, a lancet assembly receiver 206 for receiving lancet-test strip combination 100, a lancet drive mechanism 220, an activating member 240, and a trigger 208. Lancet penetration gauge 204 includes a plurality of recesses 205 each having a different depth that are configured to cooperate with a stop 218 of the lancet drive mechanism 220 for regulating the penetration depth of lancet tip 50. Housing 202 includes rails 212 having a first rail portion 214 and a second rail portion 216 offset from the first rail portion 214 as well as a receiver slot 201 (not shown) configured to align with the lancet enclosure slot 26. To set the penetration depth, lancet penetration gauge 204 is turned to align the selected recess 205 that corresponds to the depth of penetration of the lancet tip 50 desired with the position of stop 218 on second rail portion 216.

Figure 11:
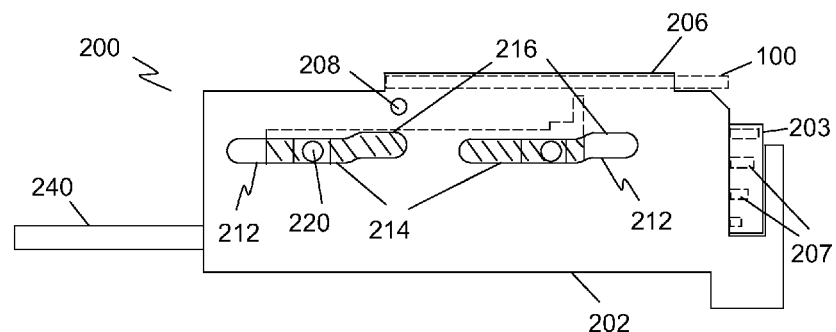
FIG. 11 is a side view of another embodiment of a lancet gun device showing a front mounted lancet penetration gauge.

FIG. 11 shows another embodiment of lancet gun device 200 with an alternate configuration for the lancet penetration gauge. The same reference numerals are used to reference the same components. The alternate configuration for the lancet penetration gauge includes a penetration gauge wheel 203 having a plurality of gauge recesses 206. The depth of each one of the plurality of gauge recesses 206 differs and corresponds to the distance the drive mechanism 220 will drive lancet tip 50 forward.

Figure 12:
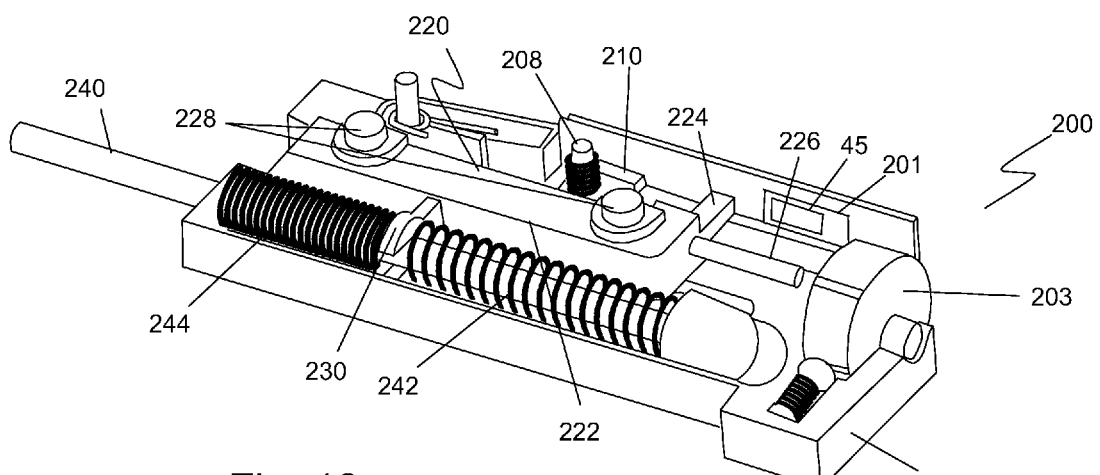
FIG. 12 is a cut-away perspective view of the lancet gun device shown in FIG. 11.

FIG. 12 shows a cutaway view of the lancet gun device 200 illustrated in FIG. 11. Lancet drive mechanism 220 includes a drive mechanism body 222, drive mechanism guides 228, a drive mechanism stop rod 226, a lancet driver 224, and spring plate 230. Drive mechanism guides 228 cooperate with housing rails 212 to guide the movement of drive mechanism body 222. Lancet driver 224 engages lancet slot 45 through housing slot 201 and lancet enclosure slot 26 to drive the lancet tip 50 out of the lancet assembly 10 and into the skin. The depth of lancet penetration is determined by the cooperation between the stop rod 226 and the selected recess 206 of penetration gauge 203 chosen. Spring plate 230 slides along activating member 240 between a return spring 242 and a drive spring 244. In the preferred embodiment in FIG. 10, stop 218 is configured on the side of at least one of the drive mechanism guides 28 that corresponds with the positioning of depth penetration gauge 204.

Figure 13:
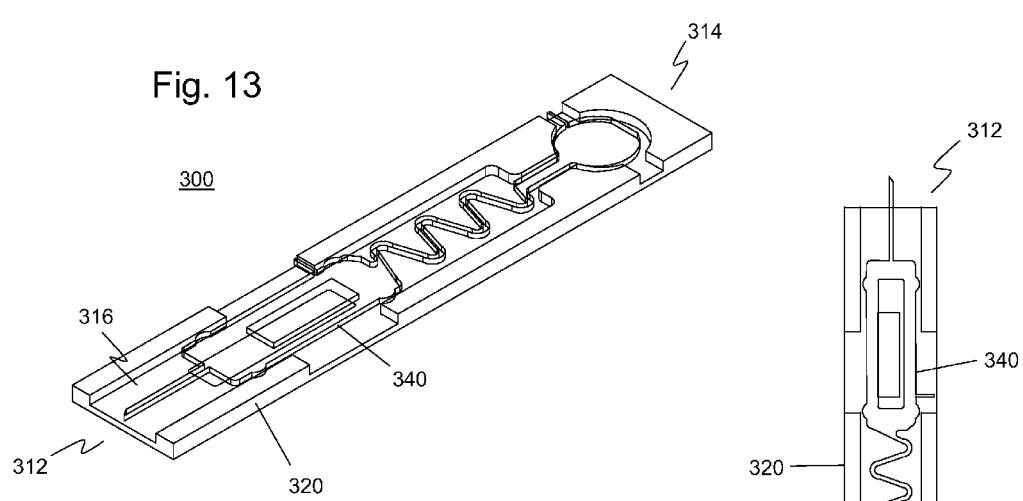
FIG. 13 is a transparent perspective view of another embodiment of the present invention showing the lancet assembly.

FIG. 13 shows another embodiment of the present invention. Lancet assembly 300 includes a lancet enclosure 320 and a lancet 340. Lancet enclosure 320 includes a recessed portion 316 that is configured to receive and contain lancet 340 when lancet assembly 300 is in a static state. Lancet assembly 300 has a needle end 312 through which lancet 340 protrudes and retracts during use and an anchor end 314. A separate lancet cover (not shown) or a test strip (discussed later) may optionally be included, but is not necessary, with the lancet enclosure 320.

Figure 14:
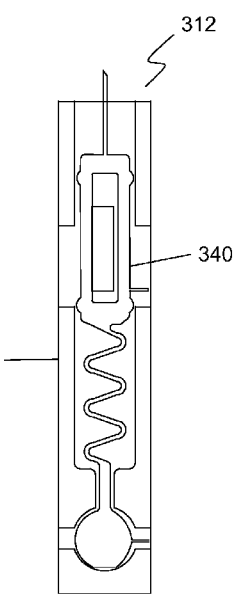
FIG. 14 is a top view of the present invention illustrated in FIG. 13.

FIG. 14 shows a top view of lancet assembly 300 during a dynamic state when lancet 340 is protruding out of open end 312 of lancet assembly 300. It should be understood that lancet 340 may be disposable and lancet enclosure 320 may be reusable or may be a part of the lancet gun device used with lancet 340.

Turning now to FIG. 15, there is shown an enlarged top view of lancet enclosure 320 of the present invention. Lancet enclosure 320 has recess portion 316 having a first recess portion 322 extending from needle end 312, a bottom 324 with a slot 326 spaced from needle end 312, a second recess portion 328 that is narrower than first recess portion 322 and which extends from first recess portion 322, and a third recess portion 330 that is wider than second recess portion 328 and which extends from second recess portion 328. Optionally, lancet enclosure 320 may have a plurality of first side openings 332 and a plurality of second side openings 334 to accommodate optional side tabs on lancet 340 that may be created during the manufacturing process. FIG. 16 is a side view of lancet enclosure 320 in FIG. 15 taken along arrows 16' and 16". First side opening 332 and second side opening 334 are more clearly depicted as being portions of lancet enclosure 320 where sections of the wall of recess 316 are absent. Typically, the thickness of lancet enclosure 320 is about 0.018 inches (0.457 mm). The depth of recess 316 is typically 0.012 inches (0.305 mm).

FIG. 17 shows an enlarged top view of lancet 340. Lancet 340 includes a lancet body 342, a lancet tip 350, a sinuous portion 355, and an anchor portion 360. Lancet body 342 has a lancet tip end 343, a sinuous portion end 344, and a slot 345. Slot 345 is configured to align with slot 326 of lancet enclosure 320 but is shorter than slot 326. This ensures sufficient clearance for a lancet driver to operate properly in conjunction with lancet assembly 300 during use. The lancet driver is inserted into slot 345 and drives lancet 340 to an extended position.

Optionally along each side 346 of lancet body 342 are located one or more lancet body protrusions 347. Lancet body protrusions 347 are optionally included to reduce the friction that arises between the sides 346 of lancet body 342 and the side walls of recess 316 during use of lancet 340. Sinuous portion 355 has a zigzag shape with a sinuous neck extension 357. Sinuous portion 355 is connected on one end to lancet body 342 and to anchor portion 360 by way of sinuous neck extension 357. Lancet 340 is preferably made of a metal material such as, for example, stainless steel having a thickness of about 0.010 inches (0.254 mm). The thickness of lancet 340 must be thinner than the depth of recess 316 in lancet enclosure 320 to allow the protrusion and retraction of lancet tip 350. Lancet 340 may also be made of other materials such as, for example, plastics having sufficient rigidity to act as a lancet tip 350 for piercing skin but be resilient enough to provide the spring-like action of the sinuous portion 355.

When assembled, lancet tip 350, lancet body 342 and sinuous portion 355 reside within first recess portion 322 of lancet enclosure 320. Sinuous neck extension 357 resides in second recess portion 328 and anchor portion 360 resides in third recess portion 330. Because second recess portion 328 is narrower than either first and third recess portions 322 and 330, respectively, third recess portion 330 holds anchor portion 360 during use as the rest of lancet 340 extends out of and retracts back into lancet enclosure 320.

Sinuous portion 355 provides a spring-like characteristic to the lancet body 342. As lancet body 342 is extended during the skin-piercing dynamic action of lancet 340, the sinuous portion 355 provides the resiliency needed to extend lancet tip 350 out of lancet enclosure 320 during use without breaking and to retract lancet tip 350 back into recess 316 of lancet enclosure 320. In this way, a user is protected from lancet tip 350 before and after use.

It should be noted that this embodiment of lancet 340 also includes lancet tabs 365. Lancet tabs 365 are the connecting material that connects one lancet 340 to another lancet 340 during mass production of lancet assembly 300. It is less expensive to leave tabs 365 on lancet 340 than to remove them. If tabs 65 are not removed, then lancet enclosure 320 requires side openings 332 and 334 in order to accommodate tabs 365 during assembly and use of lancet assembly 300. However, it should be understood by those skilled in the art that if tabs 365 are removed or if lancet 320 is made as an individual piece, then side openings 332 and 334 are also not required and may be optionally included or not.

Figure 18:
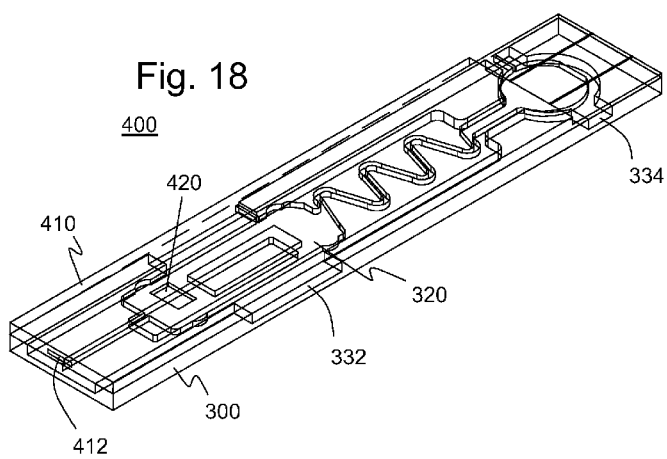
FIG. 18 is a perspective view of the embodiment of the present invention illustrated in FIG. 13 showing a test strip affixed to the lancet assembly forming a disposable lancet-test strip combination.
Figure 19:
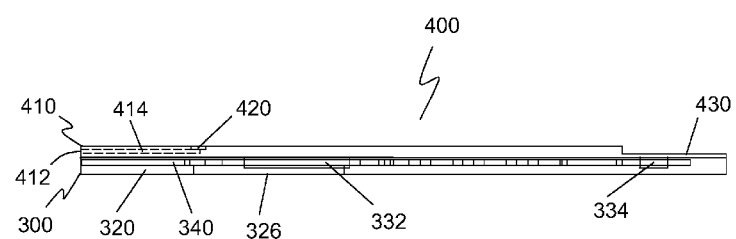
FIG. 19 is a side view of the embodiment illustrated in FIG. 18.

Turning now to FIG. 18, there is illustrated an integrated lancet-test strip combination 400 that includes lancet assembly 300 attached to a test strip 410. Test strip 410 includes a sample fluid entrance port 412, a sample chamber 414 (not shown) containing at least one sensor and a sample vent hole 420. Electrical contacts 430 are situated at the opposite end adjacent anchor end 314. Test strip 410 is preferably fixed to lancet assembly 300 forming an integrated lancet-test strip combination 400. Test strip 410 acts as a cover to recess 316 of lancet assembly 300 enclosing lancet 340 within lancet enclosure 320. FIG. 19 illustrates a side view of lancet-test strip combination 400. Sample chamber 314 is shown as a series of dashed lines between sample fluid entrance port 412 and sample vent hole 420.

To operate the lancet gun device 200, a lancet assembly 10 is loaded into lancet receiver 206. The depth of penetration of the lancet tip 50 is selected by rotating penetration gauge 204 to the desired setting. Activating member 240 is pulled away from housing 202 causing the drive spring 244 to compress while return spring 242 on activating member 240 pushes against spring plate 230 sliding lancet drive mechanism 220 into a loaded position arming trigger 208. Trigger 208 has catch 210 that holds lancet drive mechanism 220 in the loaded state until trigger 208 is fired. After arming the lancet gun device 200, activating member 240 is released and returns to its original position by return spring 242 while lancet drive mechanism 220 remains in the loaded position. As trigger 208 releases lancet drive mechanism 220, drive spring 244 quickly expands pushing against spring plate 230 driving lancet drive mechanism 220 at a relative high rate of speed.

As lancet drive mechanism 220 is released, rails 212 guide lancet drive mechanism 220 along a path that causes lancet driver 224 of drive mechanism 220 to move up through housing slot 201, lancet enclosure slot 26 and into lancet slot 45 to engage lancet body 42. As lancet drive mechanism 220 continues along the rails 212 moving from first rail portion 214 to second rail portion 216, lancet driver 224 drives lancet tip 50 towards its intended target. Lancet tip 50 penetrates the target to a predetermined depth as stop 218 engages the pre-selected recess 205 on penetration gauge 204. The return force of the impact of stop 218 against the end of recess 205 along with the spring-like action of the sinuous portion 55, which was stretched by the lancet driver 224 during the discharge of drive spring 244, causes the lancet tip 50 and lancet body 42 to return to its released, steady-state position. While returning to a steady-state position, lancet driver 224 retracts from lancet 40 disengaging with lancet, lancet enclosure and housing slots 45, 26 and 201, respectively, aided by return spring 242, which was compressed by spring plate 230 during discharge of drive spring 244.

It should be noted that lancet gun device 200 may be configured to accept only a disposable lancet 40, a lancet assembly 10, a lancet assembly 10 with a cover, or a lancet-test strip combination 100. The preferred embodiment as disclosed contemplates the use of a lancet-test strip combination for ease of use, reduced costs and increased dependability and reliability.

Figure 20:
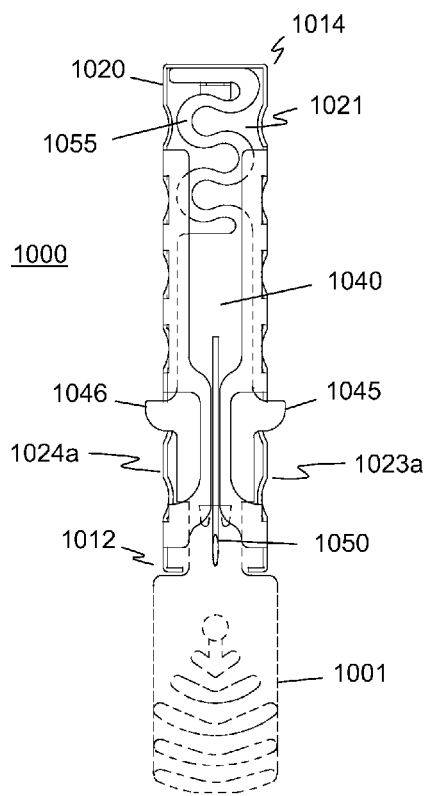
FIG. 20 is a top view of another embodiment of the lancet assembly of the present invention.

FIG. 20 shows a lancet assembly 1000 of the preferred embodiment of the present invention. Lancet assembly 1000 includes a lancet carrier 1020 and a lancet 1040. Lancet carrier 1020 includes a recess 1021 that is configured to receive and contain lancet 1040 when lancet assembly 1000 is in a static state. Lancet assembly 1000 has a needle end 1012 through which lancet 1040 protrudes and retracts during use and an anchor end 1014. Lancet 1040 has a first drive wing 1045 and a second drive wing 1046 that extend out the side of lancet carrier 1020 through side openings 1023a and 1024a, respectively. It is noted that the position of first drive wing 1045 within the opening 1023a, which extends out the opening 1023a when in the static state or the initial position, is such that the spring portion or sinuous portion 1055 cannot be compressed. A separate lancet cover (not shown) or a test strip (discussed later) may optionally be included, but is not necessary, with the lancet carrier 1020. Lancet carrier 1020 may be made of metal or a plastic material such as, for example, polyvinyl chloride, polycarbonate, polysulfone, nylon, polyurethane, cellulose nitrate, cellulose propionate, cellulose acetate, cellulose acetate butyrate, polyester, acrylic, and polystyrene. Lancet cover 1001, which is represented by dashed lines, is not part of the invention but is used only to maintain the sterility of the lance 1040 until it is used.

Figure 21:
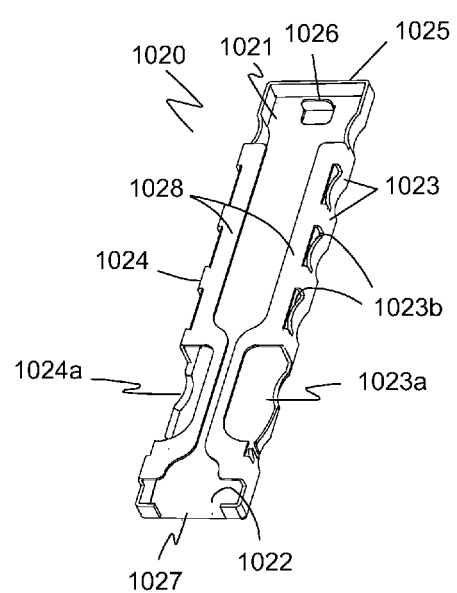
FIG. 21 is a perspective view of the lancet carrier of the embodiment shown in FIG. 20.

FIG. 21 shows one embodiment of lancet carrier 1020. In this embodiment, lancet carrier 1020 is preferably made of sheet metal, which allows lancet carrier 1020 to be stamped, cut and bent. Lancet carrier 1020 has recess 1021, a bottom 1022, a first side 1023, a second side 1024, a closed end 1025, an open end 1027, a first side opening 1023a, an optional second side opening 1024a, an anchor member 1026, and an assembly retaining mechanism 1028. First side 1023 and second side 1024 have supporting edges 1023b, 1024b, respectively, for supporting a lancet assembly cover or a sensor test strip when either one is used as part of the assembly. Assembly retaining mechanism 1028 are elongated tabs that are bent over recess 1021 to retain lancet 1040 and optional cover or test strip (not shown) when incorporated in the assembly. First side opening 1023a and optional second side opening 1024a are positioned to allow the outward extension of first drive wing 1045 and optional second drive wing 1046 through first side opening 1023a and optional second side opening 1024a, respectively, when lancet 1040 is assembled in lancet carrier 1020.

FIGS. 22A and 22B show an enlarged top view of lancet 1040. Lancet 1040 includes a lancet body 1042, a lance 1050, a sinuous portion 1055, and an anchor portion 1060 located at a sinuous portion distal end 1056. Lancet body 1042 has a lance end 1043, a sinuous portion end 1044, a first drive wing 1045, and an optional second drive wing 1046. First drive wing 1045 and optional second drive wing 1046 extend outwardly from a first side 1042a and second side 1042b, respectively, of lancet body 1042. Lance 1050 may be integrally made with lancet body 1042 or may be a separate component that is fixedly attached to lancet body 1042. A lancet driver (discussed later) cooperates with first drive wing 1045 and optional second drive wing 1046 to drive lancet 1040 to an extended position. Lancet cover 1001 is shown in FIG. 22B connected to lancet body 1042 to protect lance 1050 and maintain its sterility, and disconnected from lance body 1042 in FIG. 22A to expose lance 1050 for use.

Figure 23:
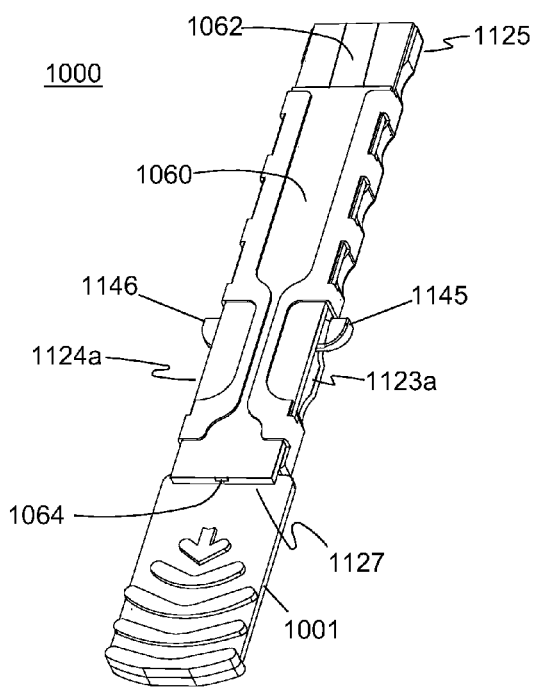
FIG. 23 is a perspective view of one embodiment of the present invention showing a lancet sensor test strip with dual drive wings.
Figure 24:
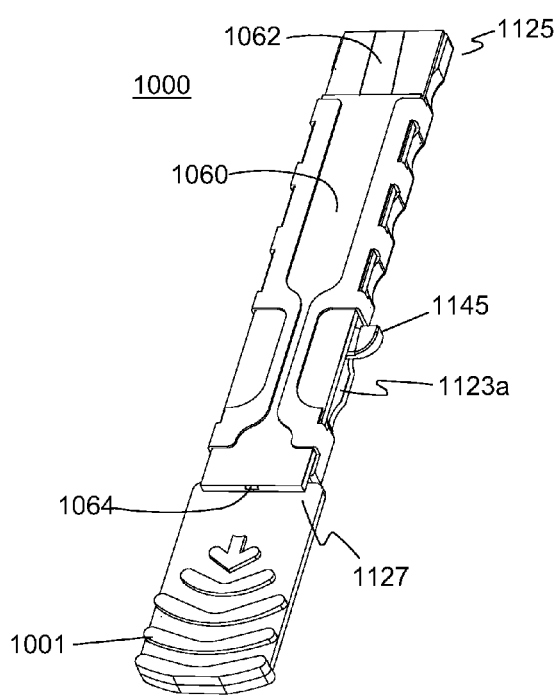
FIG. 24 is a perspective view of the embodiment shown in FIG. 23 with a single drive wing.

Turning now to FIG. 23, there is illustrated a lancet sensor assembly 1000. Lancet sensor assembly 1000 includes a lancet carrier 1120, a lancet 1140 with a first drive wing 1145 extending outwardly from a first side opening 1123a and a second drive wing 1146 extending outwardly from a second side opening 1124a, and a disposable sensor strip 1060. Disposable sensor strip 1060 has an electrical contact end 1062 over closed end 1125 and a sample receiving end 1064 over open end 1027. FIG. 24 illustrates another embodiment of lancet sensor assembly 1000 but without the optional second drive wing 1146. The remaining features are identical.

Figure 25:
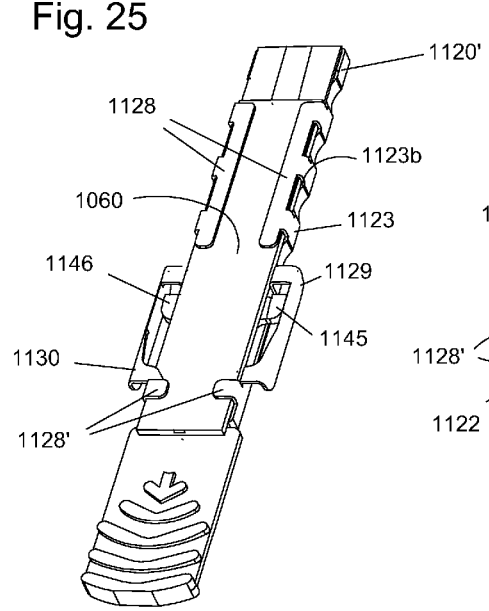
FIG. 25 is a perspective view of another embodiment of the lancet assembly of the present invention showing wing guards protecting the drive wings of the lancet.

FIG. 25 illustrates another embodiment of lancet sensor assembly 1000. Like the previously described embodiments, lancet sensor assembly 1000 includes a lancet carrier 1120', a lancet 1140 and a sensor strip 1060 combined in a single use, disposable unit. Lancet carrier 1120' includes all of the features of lancet carrier 1020 but with an additional feature. Lancet carrier 1120' includes a first wing guard 1129 and an optional second wing guard 1130. First wing guard 1129 extends over first drive wing 1145. Retaining assembly mechanism includes tabs 1128 behind first wing guard 1129 and optional second wing guard 1130 and front tabs 1128' in front of first wing guard 1129 and optional second wing guard 1130. Tabs 1128 and 1128' are bent at about 90 degrees to the side walls 1123, 1124 to secure sensor strip 1060 against supporting edges 1123b, 1124b. First wing guard 1129 protects first drive wing 1145 from being engaged or hit inadvertently when lancet sensor assembly 1000 is being handled or inserted into a meter. Optional second wing guard 1130 protects optional second drive wing 1146.

Figure 26:
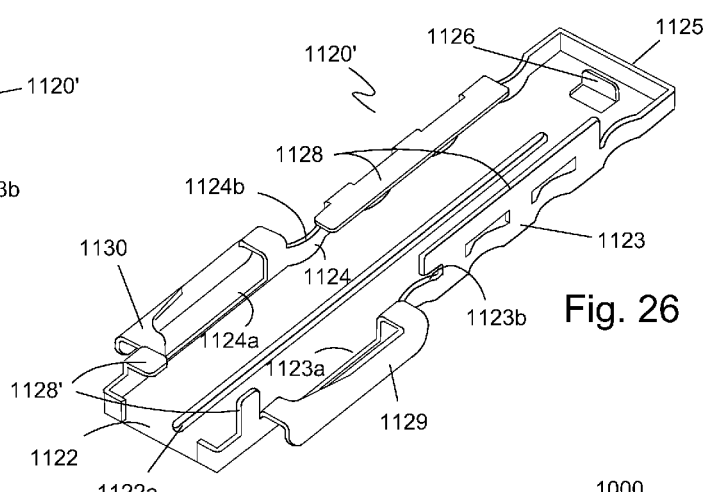
FIG. 26 is a perspective view of the elongated carrier of the lancet assembly in FIG. 25.

FIG. 26 illustrates an enlarged perspective view of lancet carrier 1120' to more clearly illustrate the features of lancet carrier 1120'. As can be seen from FIG. 26, lancet carrier 1120' includes another optional feature. The optional feature is a bottom groove 1122a in bottom 1122 that also creates a bottom rib 1122b along the outside surface 1122c of bottom 1122. Bottom groove 1122a acts as a carrier stiffener in the metal embodiment while bottom rib 1122b also provides a guiding means when the lancet sensor assembly 1000 is loaded into a handheld meter.

Figure 27:
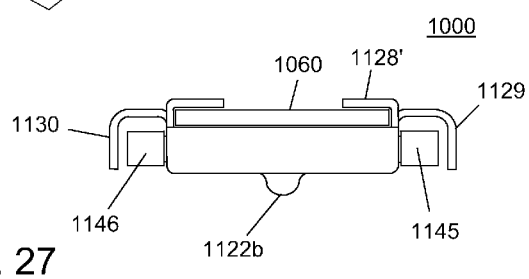
FIG. 27 is an end view of the lancet assembly in FIG. 26 showing the guide rib on the bottom of the elongated carrier.

FIG. 27 is a front end view of lancet sensor assembly 1000. Wing guards 1129 and 1130 wrap around the drive wings 1145, 1146 to protect the drive wings from being hit inadvertently when handled or inserted into a meter. Bottom rib 1122b is also shown. It should be understood that bottom rib 1122b does not have to be located along the central axis of lancet carrier 1120' in order to obtain the benefits disclosed above.

Figure 28A:
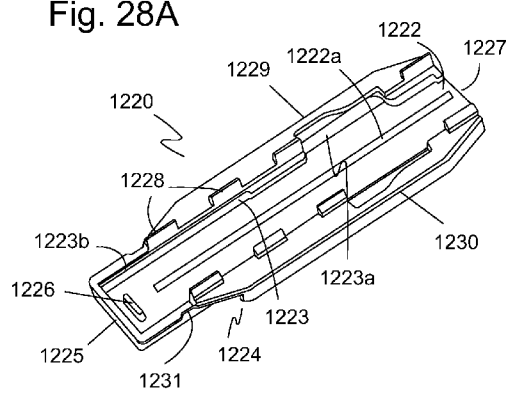
FIG. 28A is a perspective view of another embodiment of the lancet carrier of the present invention.
Figure 28B:
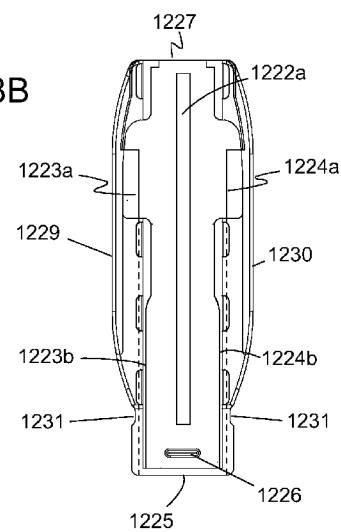
FIG. 28B is a top view of the lancet carrier shown in FIG. 28A.
Figure 28C:
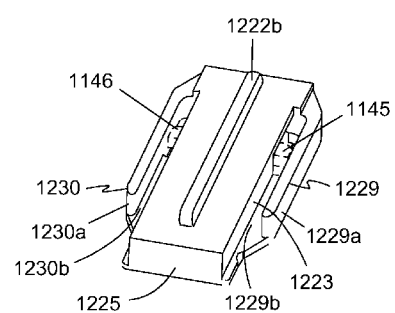
FIG. 28C is a bottom perspective view of the embodiment in FIG. 28A.

Turning now to FIGS. 28A, 28B and 28C, there is illustrated another embodiment of the lancet carrier. In this embodiment, lancet carrier 1220 is preferably made of a plastic, thermoform material that can be easily molded. Like its metal counterpart, lancet carrier 1220 includes a bottom 1222, a first side 1223, a second side 1224, a closed end 1225, an open end 1227, a first side opening 1223a, an optional second side opening 1224*a*, an anchor member 1226 located near closed end 1225, and an assembly retaining mechanism 1228. Assembly retaining mechanism 1228 are preferably a plurality of deformable tabs that are deformed to retain the test strip/cover and lancet of the assembly. First side 1223 and second side 1224 have supporting edges 1223*b*, 1224*b*, respectively, for supporting a lancet assembly cover or a sensor test strip. Lancet carrier 1220 also includes optional first wing guard 1229 and optional second wing guard 1230. Bottom 1222 may include optional bottom groove 1222*a*. In this embodiment, optional side notches 1231 are included near closed end 1225 to provide additional retention means for retaining the lancet sensor assembly when inserted into the meter. It should be understood that optional first and second wing guards 1229, 1230 may be any length and do not need to "wrap around" the drive wings. Wing guards 1229, 1230 need only extend over the drive wings sufficient to prevent the drive wings from being inadvertently hit by the user or the meter when being inserted. FIG. 28B illustrates a top view of lancet carrier 1220 with the above described features.

FIG. 28C is a bottom, perspective view of lancet carrier 1220. Lancet 1220 has optional bottom rib 1222*b* for use as a guiding means when inserting the lancet sensor assembly into a meter. Wing guards 1229, 1230 include wing driver channels 1229*b*, 1230*b* when optional wing guard side walls 1229*a*, 1230*a* are included. Wing driver channels 1229*b*, 1230*b* are formed between wing guard side walls 1229*a*, 1230*a* and first and second sides 1223, 1224. Drive wings 1145, 1146 are shown with dashed lines to provide their relative position when lancet 1040 is assembled into lancet carrier 1220. Wing driver channels 1229*b*, 1230*b* can also be used as guiding means when inserting the lancet sensor assembly into a meter.

Figure 29:
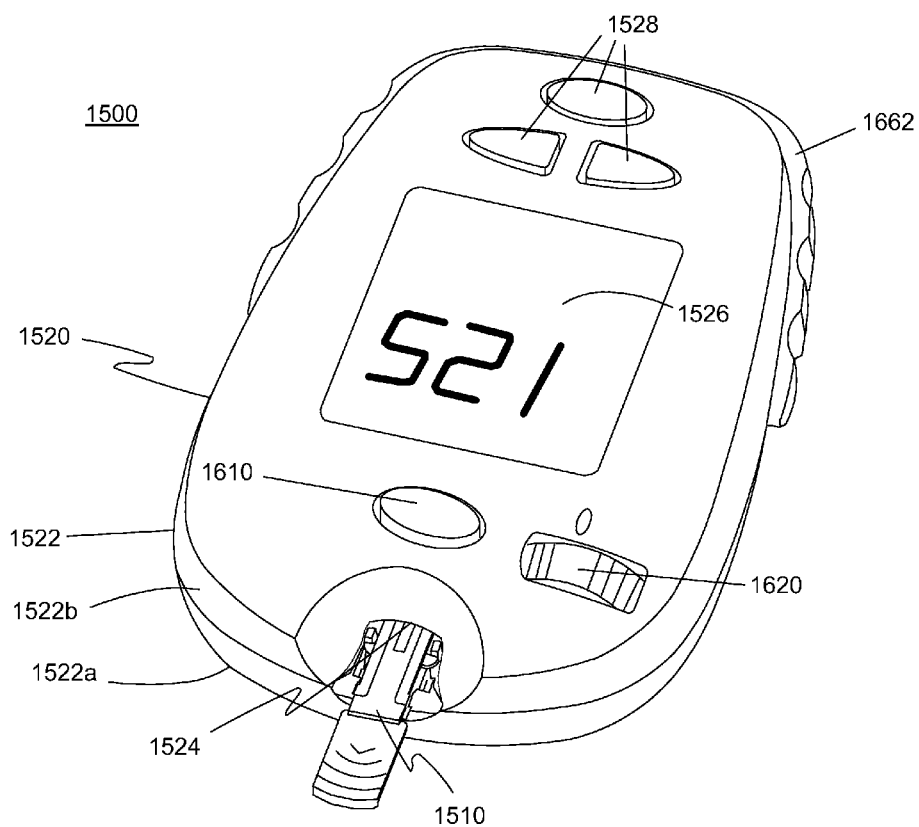
FIG. 29 is a perspective view of one embodiment of the glucose measuring system of the present invention showing the portable meter with a disposable lancet sensor test strip inserted into the test strip port.

Turning now to FIG. 29, there is illustrated a blood glucose test system 1500. Test system 1500 includes a lancet sensor strip assembly 1510 and a handheld, portable, electrochemical measuring instrument/meter 1520. Lancet sensor strip assembly 1510 is similar to the previously described strip assemblies. Portable meter 1520 includes a meter housing 1522 with a housing body 1522*a* and a housing cover 1522*b*, a test strip socket 1524, an electronic measuring circuit (not shown), a lancet driver charging system handle 1662, a display 1526, a plurality of meter measurement controls 1528, a lancet trigger 1610, and an optional lancing depth control 1620. Meter 1520 is typically battery powered for portability.

Figure 30:
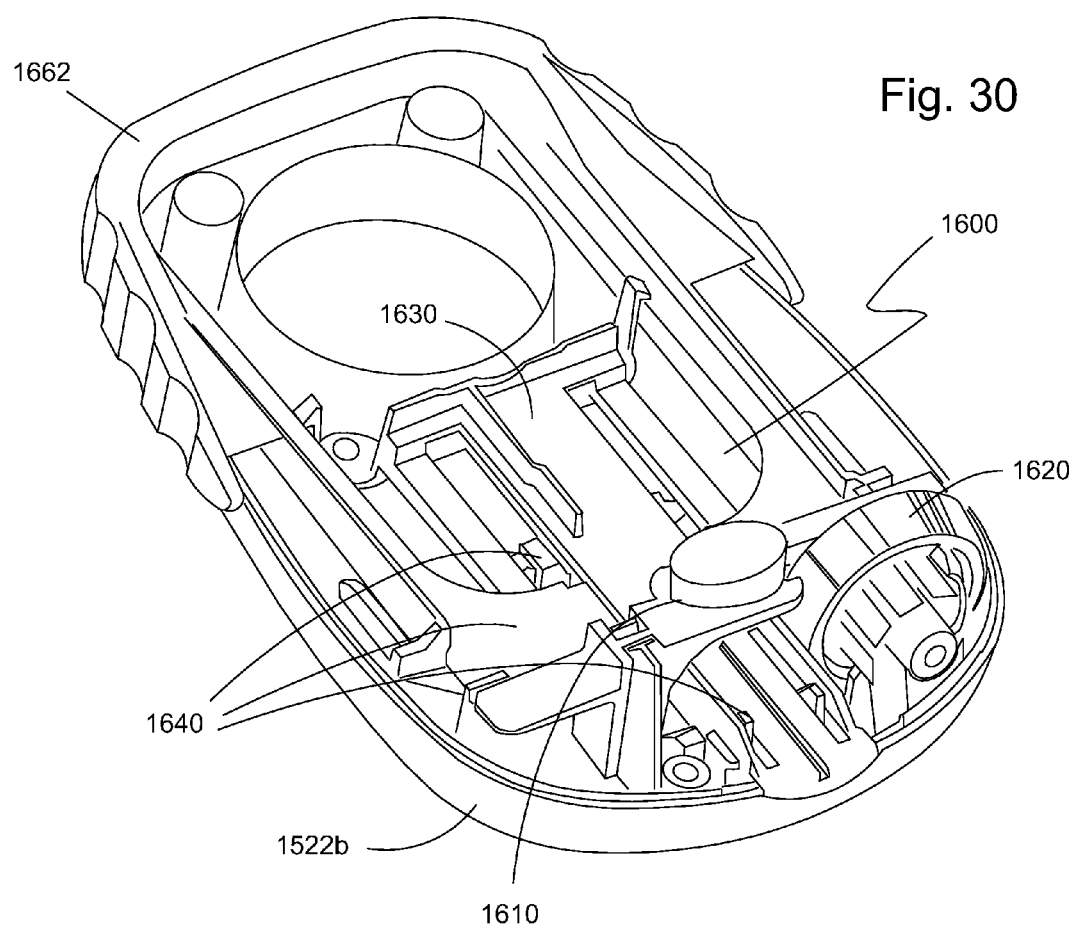
FIG. 30 is a simplified, perspective view of the inside of the meter showing one embodiment of the lancing device components.

FIG. 30 is an enlarged, simplified, perspective view of the inside of meter 1520 with the housing cover 1522*b* removed showing only the unique lancet driver assembly components 1600 within housing body 1522*a* for clarity. Lancet driver assembly components 1600 include the lancet trigger 1610, the optional lancing depth control 1620, a test strip receiver platform 1630, and a lancet driver 1640.

Figure 31A:
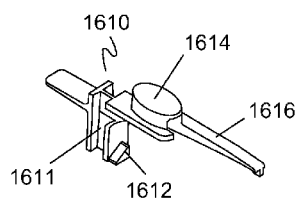
FIG. 31A is a perspective view of the lancet trigger of the embodiment in FIG. 30.

FIGS. 31A-D show each of the lancet driver assembly components 1600 separated for clarity. FIG. 31A is a perspective view of lancet trigger 1610. Lancet trigger 1610 is an asymmetrical trigger having a trigger body 1611, a drive piston release 1612 positioned near the base of trigger body 1611, and a user interface 1614 positioned on a trigger arm extension 1616 that extends outwardly from the top of trigger body 1611. When assembled, user interface 1614 is located along the central axis of the meter 1520, which coincides with the central axis of lancet sensor strip assembly 1510.

Figure 31C:
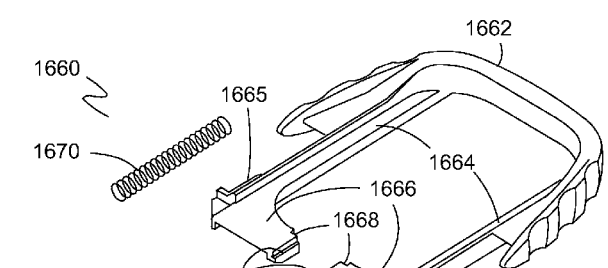
FIG. 31C is a perspective view of the lancet driver of the embodiment in FIG. 30.
Figure 31B:
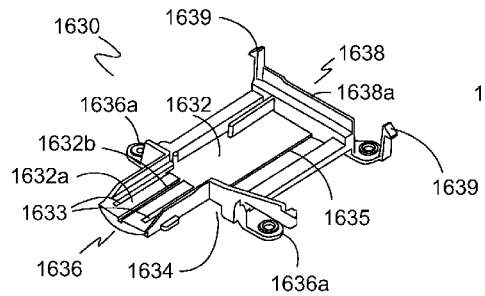
FIG. 31B is a perspective view of the test strip receiver platform of the embodiment in FIG. 30.

FIG. 31B is a perspective view of test strip receiver platform 1630. Test strip receiver platform 1630 has a first platform side 1632, a second platform side 1634, a platform proximal end 1636, and a platform distal end 1638. First platform side 1632 includes a test strip support surface 1632*a* beginning at platform proximal end 1636 for a pre-determined distance toward platform distal end 1638. Test strip support surface 1632*a* includes an optional guide groove 1632*b* configured for receiving optional bottom rib 1022*b* or 1222*b* of lancet carrier 1020, 1200, respectively. Platform proximal end 1636 is supported at test strip port 1524 of meter 1520 by a pair of proximal end legs 1636*a*. Distal platform end 1638 includes a cross support 1638*a* with a guide hook 1639 on each end. Test receiver platform 1630 also includes at least one driver slot 1633 parallel to the guide groove 1632*b* and an elongated guide surface 1635 for sliding cooperation with driver charging member 1660.

FIG. 31C is a perspective view of lancet driver 1640. Lancet driver 1640 includes a driver piston 1642 and a driver charging member 1660. Driver piston 1642 has a piston body 1643 with a drive wing end 1644 having at least one lancet driver surface 1645, a drive spring recess 1646, a pair of return spring arms 1648 extending away from and perpendicular to driver body 1643, a piston drive spring 1647, and a pair of piston return springs 1649. Driver piston 1642 is positioned adjacent second platform side 1634 with lancet driver surface 1645 extending through driver slot 1633 of test strip receiver platform 1630 for engagement with drive wing 1145 of lancet 1040. Driver piston 1642 also includes a driver piston holding surface 1652 that cooperates with driver piston release 1612 to hold driver piston 1642 in an "armed" position. Drive spring recess 1646 secures piston drive spring 1647 on one end and the other end of piston drive spring 1647 contacts a central portion of cross support 1638*a* of test receiver platform 1630. A piston return spring 1649 is positioned on each side of piston body 1643 between proximal end legs 1636*a* of test strip platform 1630 and the return spring arms 1648. Each return spring arm 1648 includes a charging contact stop surface 1650.

Figure 31D:
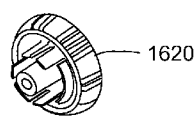
FIG. 31D is a perspective view of the depth gauge control of the embodiment in FIG. 30.

Driver charging member 1660 has a charging system handle 1662, a pair of parallel, charging member rails 1664 extending from the inside of handle 1662, charging member arms 1666 located distally from charging member handle 1662 and extending perpendicularly from the inside of each charging member rail 1664 towards each other, a stop interface 1669 on an end of one of the charging member arms 1666, and a pair of charging member return springs 1670. Each of the charging member return springs 1670 connects on one end to a charging member arm spring receiver 1665 located on the outside of the charging member arm 1666 and on the other end to the inside of meter housing 1520. Charging member rails 1664 slidingly support the guide hooks 1639 of test strip platform 1630. Each charging member arm 1666 has a test strip platform rail 1667 that slidingly engages with one of the platform side edges 1635. Charging member arm 1666 also includes a piston stop surface 1668 that is used to arm drive piston 1642 by engaging against charging contact stop surface 1650. Piston stop surface 1668 also stops the sliding movement of drive piston 1642 when the armed lancet driver 1640 is discharged. FIG. 31D is a perspective view of optional lancing depth control 1620. Lancing depth control 1620 is more fully illustrated in FIGS. 32A, B and C.

Figure 32A:
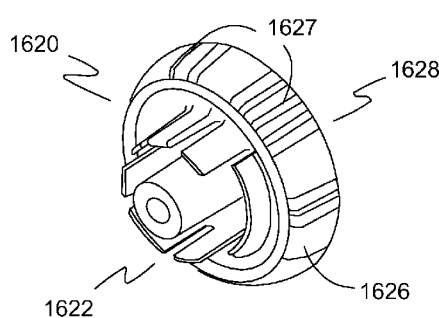
FIG. 32A is a front, perspective view of one embodiment of the optional depth gauge control of the present invention.

FIG. 32A illustrates a perspective view of lancing depth control 1620. Lancing depth control 1620 is considered optional since the lancet driver could be made for a single lancing depth. Lancing depth control 1620 includes a detent side 1622 and a depth gauge side 1628. The preferred shape of lancing depth control 1620 is a wheel having an outer peripheral surface 1626. Outer peripheral surface 1626 may include indicia 1627 to indicate relative depth of penetration of the lance. Detent side 1622 includes a plurality of extending tabs 1624.

Figure 32C:
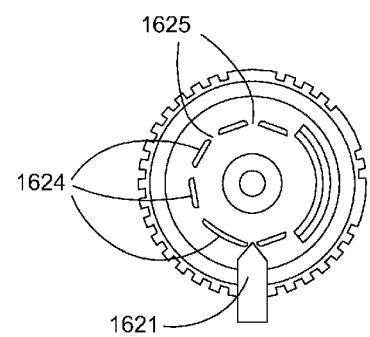
FIG. 32C is a frontal view of the embodiment of the optional depth gauge control shown in FIG. 32A.
Figure 32B:
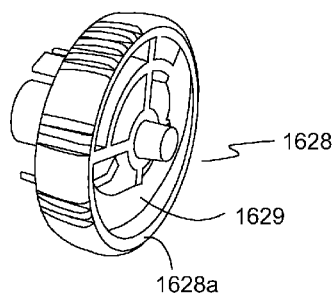
FIG. 32B is a back, perspective view of the embodiment of the optional depth gauge control in FIG. 32A.

FIG. 32B shows depth gauge side 1628 with a charging member interface surface 1629. Charging member interface surface 1629 is a gradually, recessing, circumferential surface that has a variable distance between the interface surface 1629 and the back surface 1628a of lancing depth control 1620. Charging member interface surface 1629 cooperatively engages with stop interface 1669 of driver charging member 1660 to set the lancing depth for lance 1050.

FIG. 32C is a front view of lancing depth control 1620. Extending tabs 1624 are space along the detent side 1622 to coincide with a pre-determined lancing depth for lance 1050. The tab spaces 1625 are important for engaging a detent 1621 to temporarily lock the position of lancing depth control 1620. Detent 1621 may be a separate structure or may be integrally formed on the inside of meter housing 1520. Extending tabs 1624 are relatively rigid but have sufficient flexibility to allow the tabs to ride over detent 1621 when lancing depth control 1620 is re-positioned for a different lancing depth. Extending tabs 1624 return to their original position when detent 1621 enters a tab space 1625 to temporarily set and temporarily lock the lancing depth control 1620 to the desired lancing depth.

To determine the blood glucose level of a user, blood glucose test system 1500 requires a lancet sensor strip assembly 1510 and the handheld meter 1520. To make the measurement, lancing depth control 1620 is set to the preferred lancing depth. The charging handle 1662 is pulled away from meter housing 1520. This action causes the piston stop surface 1668 of the charging member arms 1666 to engage charging contact stop surface 1650 of driver piston 1642 pulling driver piston 1642 toward an "armed" position and causing the piston drive spring 1647 to compress against cross support 1638a of test receiver platform 1630. As driver piston 1642 is pulled toward cross support 1638a, driver piston holding surface 1652 engages drive piston release 1612 of lancet trigger 1610 to hold driver piston 1642 in the "armed" position. When the charging handle 1662 is released after arming the driver piston 1642, the charging member return springs 1670 returns the charging handle 1662 to its original position with the stop interface 1669 resting against the charging member interface surface 1629 of lancing depth control 1620.

A lancet sensor test strip 1510 is inserted into test strip port 1524 of meter 1520 and the protective lancet cover 1001 is pulled away from the test strip. It should be noted that "arming" the driver piston 1642 may be performed after the lancet sensor test strip 1510 is inserted into test strip port 1524. The end of lancet sensor test strip 1510 is placed against the user's skin where the lancing is to be performed. Once in position, the user simply pushes the lancet trigger 1610 releasing the driver piston 1642. As the driver piston 1642 moves, lancet driver surface 1645 engages drive wings 1145, 1146 causing the lance 1050 to extend out of lancet carrier 1020 piercing the user's skin. Driver piston 1642 stops when charging contact stop surface 1650 hits piston stop surface 1668 of charging member 1660. Piston return springs 1649 cause piston driver 1642 to return to its discharged/resting position. Once drive wings 1145, 1146 are released, the spring action of sinuous portion 1055 causes lance 1050 to retract back into lancet carrier 1020.

The user then removes the meter and strip from the wound site and massages or "milks" the wound site to generate sufficient sample for testing. The penetration depths of lance 1050 are purposely selected for pain-free lancing. Because the penetration depth of lance 1050 is so shallow, massaging or "milking" the wound site is necessary to obtain sufficient sample for testing. Once a sufficiently sized blood droplet appears, the meter and strip are returned to the wound site to allow the sample to enter the sample chamber of the sensor test strip. The meter then electrochemically determines the concentration of glucose in the blood from the blood sample. Once the measurement is complete, the disposable lancet sensor strip 1510 is removed from meter 1520.

It should be understood that the blood glucose test system 1500 may be configured to use anyone of the electrochemical methods used for determining the concentration of glucose in a sample. For example, these methods include amperometric, coulometric, potentiometric, voltammetric, and other electrochemical techniques.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A method of obtaining a test sample from a specimen using a lancet system comprising:
engaging a lancet driver against a drive wing of a lancet system, the lancet system having a major portion of a lancet member slidably engaged within a lancet carrier and a sensor strip with a sample chamber attached to the lancet carrier, the lancet system having a lance connected to a first end of a lancet body of the lancet member wherein the lance is movable from a retracted position within the lancet carrier to an extended position outside the lancet carrier, the drive wing extending outwardly and transversely from the lancet body, the major portion of the lancet member having a sinuous portion with a distal end restricted from movement by the lancet carrier, the sinuous portion being non-compressible when initially disposed within the lancet carrier wherein the drive wing prevents the sinuous portion from being compressed;
moving the drive wing with the lancet driver a predetermined distance causing a lancet tip to move from the retracted position to the extended position; and
disengaging the lancet driver from the drive wing, the lance being automatically moved from the extended position to the retracted position.

2. The method of claim 1 further comprising massaging a lanced specimen to generate a sample sufficient for disposing within a sample chamber of a sensor strip connected to the lancet carrier and moving the sensor strip to the sample for receiving a portion of the sample within the sample chamber.

3. The method of claim 1 further comprising arming the lancet driver before engaging the drive wing.

4. A method of measuring blood glucose using a lancet system comprising a portable meter and a lancet assembly, the method comprising:
charging a lancet driver to an armed positioned wherein the lancet driver is incorporated within the portable meter;
inserting a lancet assembly into a lancet assembly port on the meter until the lancet assembly engages a test strip connector within the meter and electrically contacting a sensor strip of the lancet assembly, the lancet assembly having a lancet member that includes a lancet body with a drive wing extending outwardly from a side of the lancet body, a lance connected to one end of the lancet body, and a sinuous portion connected to a second end of the lancet body wherein a major portion of the lancet member is adapted to slide the lance between an unexposed position and an exposed position, the sinuous portion being non-compressible when initially disposed within a lancet carrier wherein the drive wing prevents the sinuous portion from being compressed;

positioning the exposed end of the lancet assembly against a user's skin;

activating the lancet driver causing a lance in the lancet assembly to lance the user's skin;

moving a lanced system away from the lanced site;

massaging the patient's skin near the lanced site to express a quantity of blood; and applying a portion of the expressed quantity of blood to a sample inlet on the sensor strip of the lancet assembly.

5. The method of claim 4 further comprising adjusting a lancing depth control of the portable meter to a selectable depth setting.

* * * * *